United States Patent
Mintah et al.

(10) Patent No.: US 9,261,481 B2
(45) Date of Patent: Feb. 16, 2016

(54) DIAGNOSTIC SYSTEM AND METHOD FOR NITROGEN OXIDE SENSOR

(71) Applicant: Caterpillar Inc., Peoria, IL (US)

(72) Inventors: Brian Y. Mintah, Washington, IL (US); Jason K. Bloms, Edwards, IL (US); Purvarag Shah, Dunlap, IL (US); Drew D. Wackerlin, Pekin, IL (US)

(73) Assignee: Caterpillar Inc., Peoria, IL (US)

( * ) Notice: Subject to any disclaimer, the term of this patent is extended or adjusted under 35 U.S.C. 154(b) by 264 days.

(21) Appl. No.: 13/836,585

(22) Filed: Mar. 15, 2013

(65) Prior Publication Data
US 2014/0260533 A1    Sep. 18, 2014

(51) Int. Cl.
*G01N 27/416* (2006.01)
*F02D 41/14* (2006.01)
*F02D 41/22* (2006.01)

(52) U.S. Cl.
CPC ........ *G01N 27/4163* (2013.01); *F02D 41/1461* (2013.01); *F02D 41/1463* (2013.01); *F02D 41/222* (2013.01); *F02D 41/1441* (2013.01)

(58) Field of Classification Search
CPC .................................................. G01N 27/4163
See application file for complete search history.

(56) References Cited

U.S. PATENT DOCUMENTS

| | | | |
|---|---|---|---|
| 6,961,653 B2 | 11/2005 | Maki | |
| 7,021,300 B2 | 4/2006 | Maki et al. | |
| 8,112,984 B2 | 2/2012 | Dietl et al. | |
| 8,190,352 B2 | 5/2012 | Brandt et al. | |
| 2004/0010364 A1 | 1/2004 | Yasui et al. | |
| 2008/0028828 A1 | 2/2008 | Iihoshi et al. | |
| 2009/0173140 A1* | 7/2009 | Sumitani | G01M 15/102 73/23.31 |
| 2009/0260429 A1 | 10/2009 | Wehmeier et al. | |
| 2010/0218487 A1 | 9/2010 | Wang et al. | |

FOREIGN PATENT DOCUMENTS

EP    DE 102011077251 B3  *  6/2012  .............. F01N 3/208

OTHER PUBLICATIONS

Non-Patent Literature "Design of a Selective Catalytic Reduction System to Reduce NOx Emissions of the 2003 West Virginia University FutureTruck", by Russell T. King, published in 2007.*

* cited by examiner

*Primary Examiner* — Daniel S Larkin
*Assistant Examiner* — Irving A Campbell

(57) ABSTRACT

A system including a nitrogen oxide sensor and a controller is provided. The nitrogen oxide sensor is configured to generate a first signal indicative of nitrogen oxides content in an exhaust gas. The controller is communicably coupled to the nitrogen oxide sensor. The controller configured to receive the first signal indicative of nitrogen oxides content in the exhaust gas. The controller is also configured to receive a second signal corresponding to an operational parameter of a power source. Further, the controller is configured to compare a derivative of the first signal with a derivative of the second signal. The controller is configured to trigger an error counter when an absolute value of the compared derivative crosses a predetermined threshold. Thereafter, the controller is configured to determine a condition of the nitrogen oxide sensor based on a count of the error counter in a predetermined period of time.

9 Claims, 4 Drawing Sheets

DIAGNOSTIC SYSTEM AND METHOD FOR NITROGEN OXIDE SENSOR

TECHNICAL FIELD

The present disclosure relates to diagnostic system and method, and more particularly to the system and method for determining an operational health of a nitrogen oxide sensor.

BACKGROUND

Conventionally, emissions requirements regulate constituents of tailpipe out emissions. Specifically, the amount of nitrogen oxide released into the atmosphere is regulated. Engines may include after treatment systems to mitigate the amount of nitrogen oxide being released into the atmosphere. The after treatment systems typically include a nitrogen oxide sensor to determine the amount of nitrogen oxide present in an exhaust stream.

However, occasionally the nitrogen oxide sensor may fail. Failure may occur due to various factors such as, for example, overheating, manufacturing defects, and the like. Typically, during operation, an output of the nitrogen oxide sensor should directly correspond to the amount of fuel used by the engine. That is, when more fuel is used by the engine, generally, more nitrogen oxide should be sensed by the nitrogen oxide sensor. Hence, the failure of the nitrogen oxide sensor can be determined based on monitoring the fuel usage and the sensed nitrogen oxide content of the exhaust stream.

For example, U.S. Published Application No. 2004/0010364 discloses an apparatus for detecting a failure of an exhaust gas sensor disposed downstream of a catalyst converter in an exhaust manifold. The apparatus comprises a control unit. The control unit determines a ratio between an amplitude value of a first output of the exhaust gas sensor and an amplitude value of a second output of an air-fuel ratio sensor. The air fuel ratio sensor is disposed upstream of the catalyst converter. The control unit detects a failure of the exhaust gas sensor based on the ratio. In one embodiment, a statistical process using a successive least squares method is applied to the ratio. The control unit detects a failure of the exhaust gas sensor based on the statistically processed ratio. In another embodiment, the statistical process is applied to both the output of the exhaust gas sensor and the output of the air-fuel ratio sensor. The control unit detects a failure of the exhaust gas sensor based on a ratio between the statistically processed outputs of the exhaust gas sensor and the air-fuel ratio sensor.

SUMMARY OF THE DISCLOSURE

In one aspect of the present disclosure, a system is provided. The system includes a nitrogen oxide sensor and a controller. The nitrogen oxide sensor is configured to generate a first signal indicative of nitrogen oxides content in an exhaust gas. The controller is communicably coupled to the nitrogen oxide sensor. The controller is configured to receive, from the nitrogen oxide sensor, the first signal indicative of nitrogen oxides content in the exhaust gas. The controller is also configured to receive a second signal corresponding to an operational parameter of a power source. Further, the controller is configured to compare a derivative of the first signal with a derivative of the second signal. The controller is configured to trigger an error counter an absolute value of the compared derivative crosses a predetermined threshold. Thereafter, the controller is configured to determine a condition of the nitrogen oxide sensor based on a count of the error counter in a predetermined period of time.

In another aspect, a diagnostic method for a nitrogen oxide sensor is provided. The method receives, from the nitrogen oxide sensor, a first signal indicative of nitrogen oxides content in an exhaust gas. The method receives a second signal corresponding to an operational parameter of a power source. Thereafter, the method compares a derivative of the first signal with a derivative of the second signal. Then, the method triggers an error counter when an absolute value of the compared derivative crosses a predetermined threshold. The method also determines a condition of the nitrogen oxide sensor based on a count of the error counter in a predetermined period of time.

Other features and aspects of this disclosure will be apparent from the following description and the accompanying drawings.

DETAILED DESCRIPTION

Figure 1:
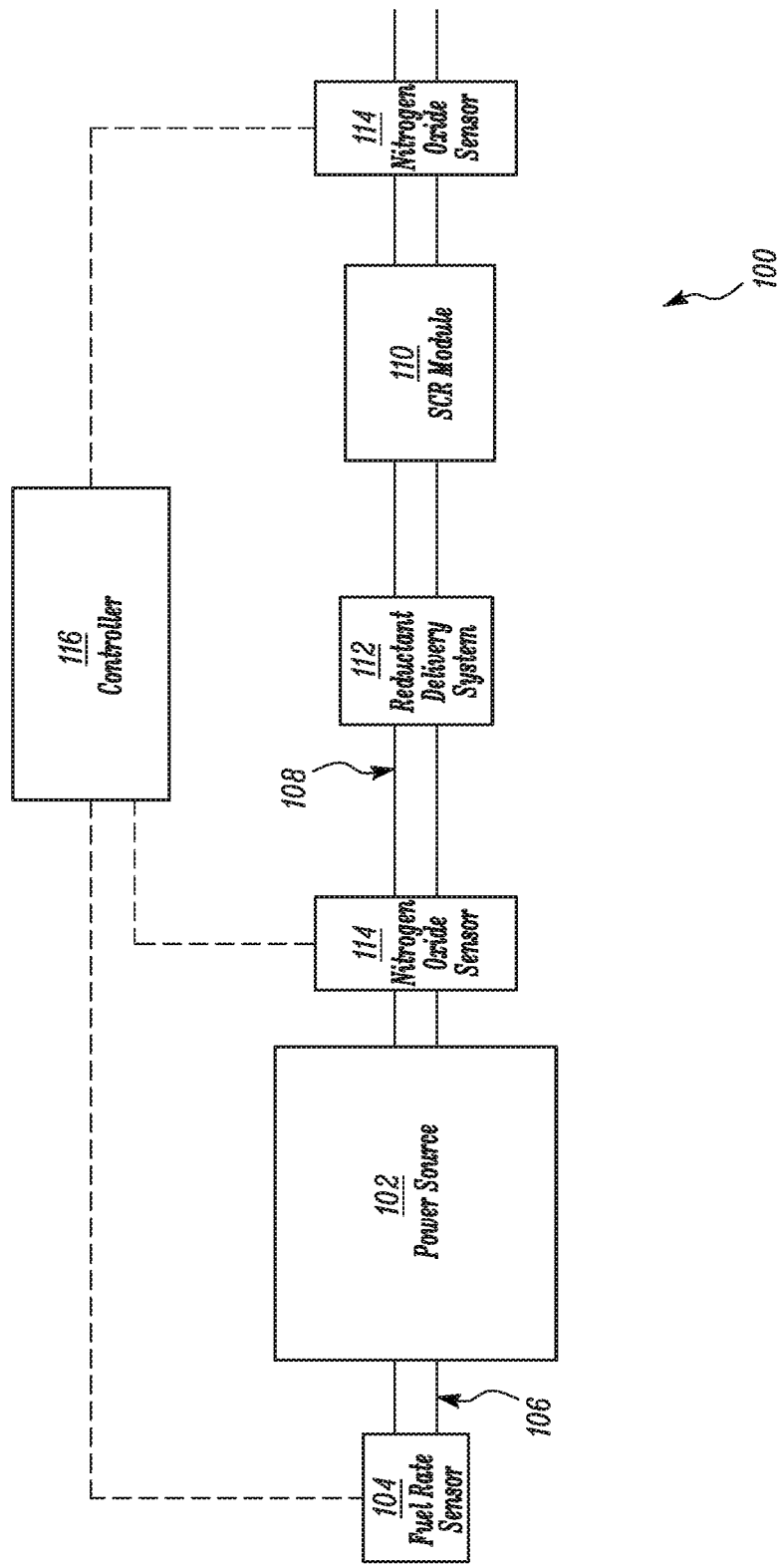
FIG. 1 is a block diagram of an exemplary system including a nitrogen oxide sensor, according to one embodiment of the present disclosure.

Wherever possible, the same reference numbers will be used throughout the drawings to refer to the same or the like parts. FIG. 1 is a block diagram of an exemplary system 100 for a power source 102. The power source 102 may include an internal combustion engine. In one example, the power source 102 is a diesel engine used in any heavy duty vehicle. A fuel rate sensor 104 may be coupled to an intake line 106 associated with the power source 102. Alternatively, the fuel rate sensor 104 may also be coupled to an intake manifold of the power source 102. The fuel rate sensor 104 may be configured to generate a signal indicative of air to fuel ratio of the fuel charge being fed to the power source 102 for combustion. The combustion of the fuel charge may take place within the power source 102, resulting in the formation of exhaust gases.

As shown, an exhaust pipe segment 108 may be connected to the power source 102. The exhaust pipe segment 108 is configured to provide a flow path for the exhaust gases exiting the power source 102. The exhaust gases may be delivered to an SCR module 110. The SCR module 110 may preferably include a base metal/zeolite formulation. A reductant, such as aqueous urea, may be stored in a reductant storage tank (not shown). Further, the reductant may be delivered to a reductant delivery system 112 coupled to the exhaust pipe segment 108 located upstream of SCR module 110. The reductant delivery system 112 may include a pump, a control valve, and an injector, such that the reductant is metered out by the pump, through the control valve and then introduced into the exhaust gas flow via the injector of the reductant delivery system 112. The exhaust gas exiting the SCR module 110 may be released into the atmosphere.

Referring to FIG. 1, an engine-out nitrogen oxide sensor 114 may be provided in the exhaust pipe segment 108 proximate to the power source 102. Moreover, a tail-pipe nitrogen oxide sensor 114 may be provided downstream of the SCR module 110. It should be noted that the term nitrogen oxide sensor 114 hereinafter refers to any one or both of the engine-out and the tail pipe nitrogen oxide sensors, based on the system. The nitrogen oxide sensor 114 is configured to generate a first signal indicative of nitrogen oxides content in the exhaust gas. A person of ordinary skill in the art will appreciate that the system 100 may include either a single nitrogen oxide sensor 114 or a plurality of the nitrogen oxide sensors 114, based on the application.

The present disclosure relates to a controller 116 which is communicably coupled to the nitrogen oxide sensor 114. The controller 116 is configured to determine a condition of the nitrogen oxide sensor 114. More particularly, the controller 116 is configured to detect a failure of the nitrogen oxide sensor 114. In one embodiment, as will be explained in detail in connection with FIGS. 2 and 3, the controller 116 is configured to detect an erratic failure of the nitrogen oxide sensor 114 or a flat-lined failure of the nitrogen oxide sensor 114.

The controller 116 is configured to receive the first signal indicative of the nitrogen oxides content in the exhaust gas from the nitrogen oxide sensor 114. An exemplary first signal generated by the nitrogen oxide sensor 114 is shown in section 202 of FIG. 2. As can be seen, the first signal is indicative of the variation of the volume of the nitrogen oxides content of the exhaust gas measured by the nitrogen oxide sensor 114 over time in an exemplary situation.

The controller 116 is further configured to receive a second signal corresponding to an operational parameter of the power source 102. In one embodiment, the operational parameter of the power source 102 may include a rate of fuel usage by the power source 102. In one embodiment, the controller 116 may receive the second signal indicative of the rate of fuel used by the power source 102, from the fuel rate sensor 104. One of ordinary skill in the art will appreciate that the controller 116 may alternatively determine the rate of fuel used by the power source 102 based on other measured or computed signals without deviating from the scope of the disclosure. Exemplary second signals received by the controller 116 from the fuel rate sensor 104 are shown in FIGS. 2 and 3, according to various embodiments of the present disclosure.

A correlation should exist between the fuel used by the power source 102 and the nitrogen oxides content of the exhaust gas measured by the nitrogen oxide sensor 114. More specifically, an output of the nitrogen oxide sensor 114 should directly correspond to the amount of the fuel used by the power source 102. This is based on the fact that the nitrogen oxides content present in the exhaust gas is a by-product of the combustion of the fuel in the power source 102. Hence, when relatively more fuel is used, the nitrogen oxides content sensed by the nitrogen oxide sensor 114 should also be more. In other words, the rate of fuel usage of the power source 102 should approximately track the output of the nitrogen oxide sensor 114. Presence of disparities in the behavior of the rate of fuel usage of the power source 102 and the output of the nitrogen oxide sensor 114 may be indicative of the failure of the nitrogen oxide sensor 114.

Figure 2:
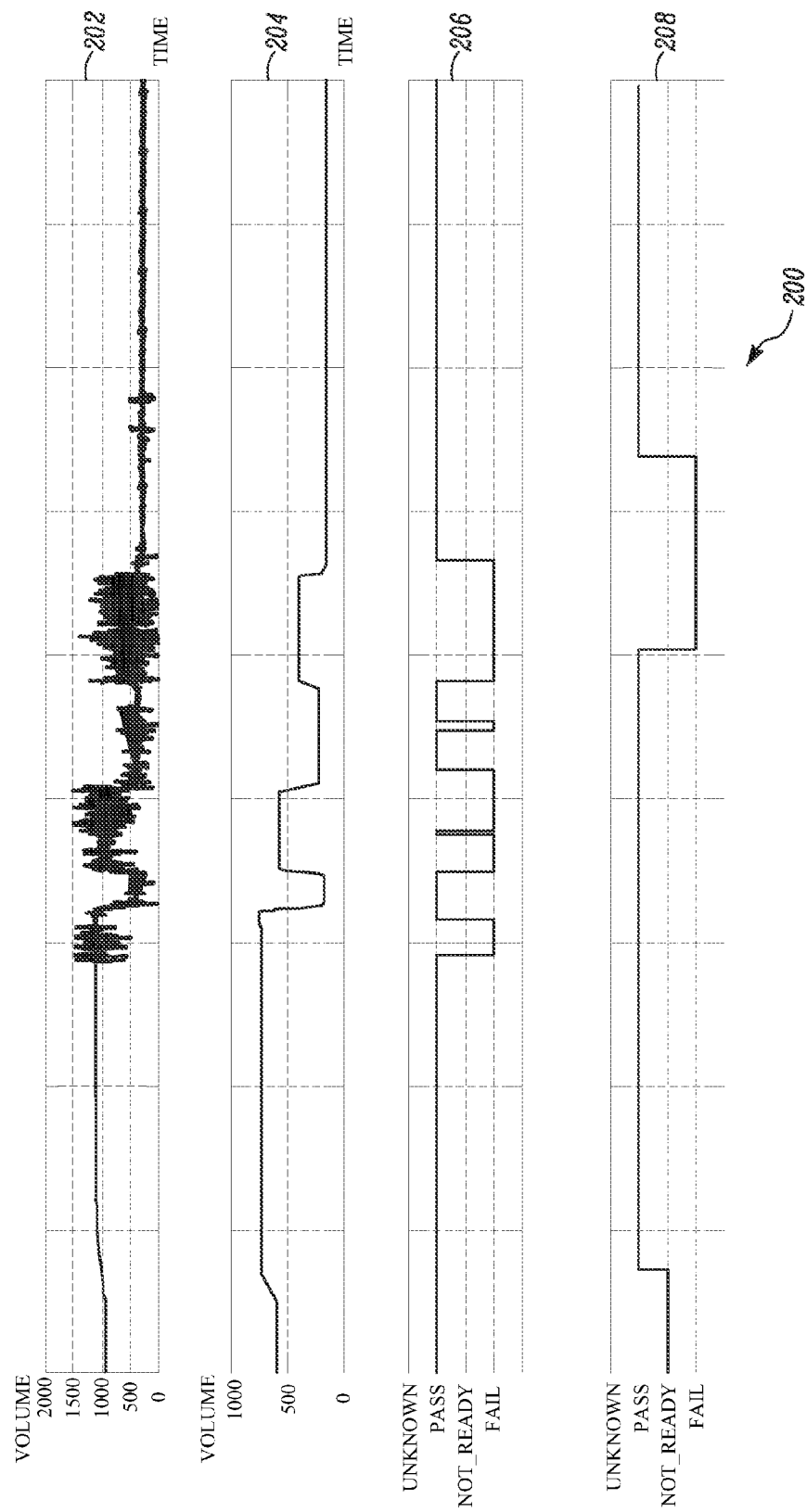
FIG. 2 is an exemplary set of graphs including a signal generated by the nitrogen oxide sensor.
Figure 3:
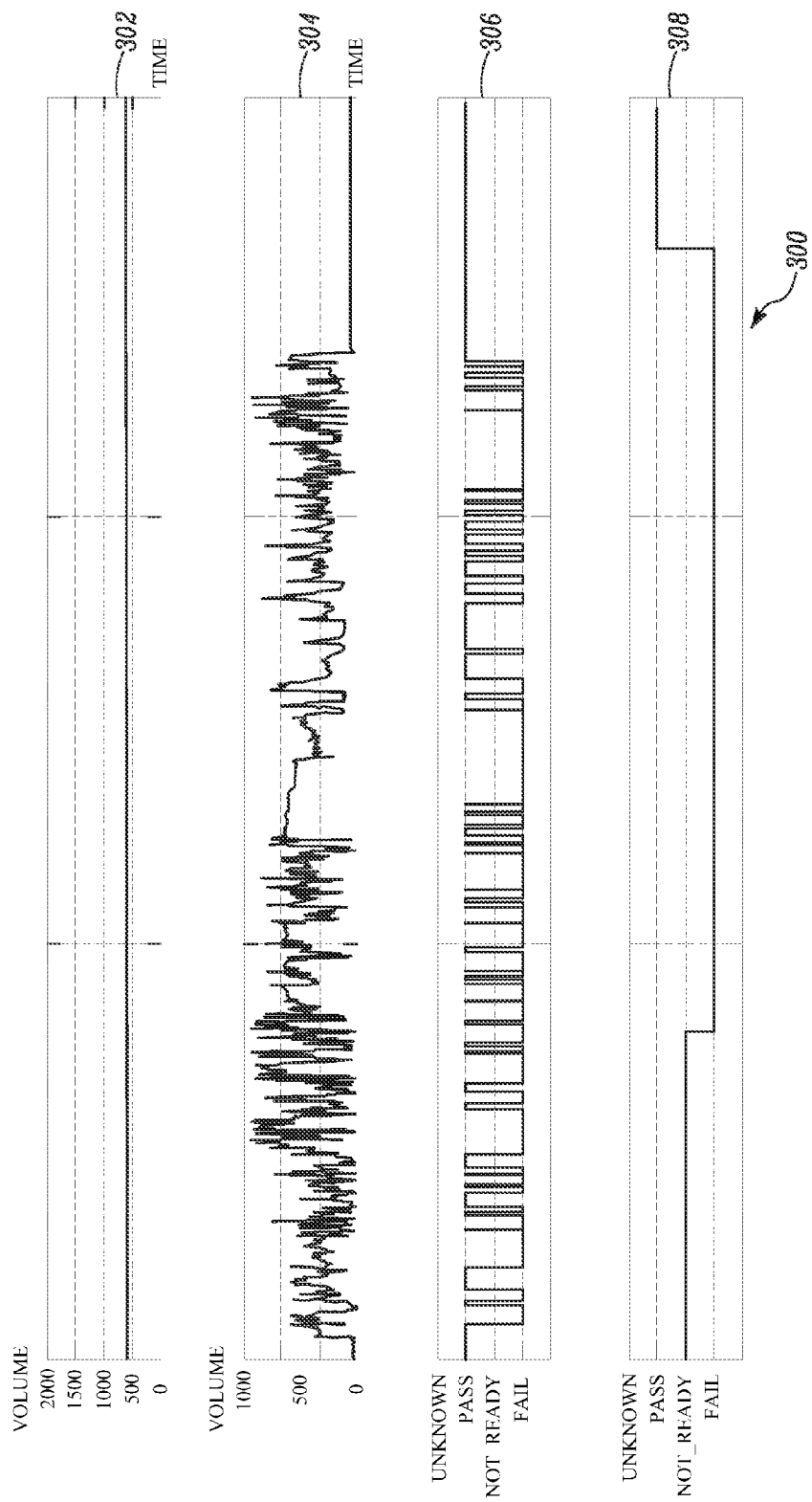
FIG. 3 is another exemplary set of graphs including the signals generated by the nitrogen oxide sensor.

In an exemplary situation, the second signal received by the controller 116 is shown in section 204 of FIG. 2. The controller 116 is configured to determine the condition of the nitrogen oxide sensor 114 based on a comparison between the first signal and the second signal. More particularly, the controller 116 is configured to determine a derivative of the first signal. The controller 116 may further determine a derivative of the second signal. Thereafter, the controller 116 is configured to compare the derivative of the first signal with the derivative of the second signal. A person of ordinary skill in the art will appreciate that comparison of the derivative of the first signal with the derivative of the second signal may facilitate in determining if the first signal and the second signal relatively track or match each other. It should be noted that a deviation in the compared signals may be ascertained when the derivative of the first and second signals cross a predetermined threshold.

The controller 116 is configured to trigger an error counter when an absolute value of the compared derivative crosses the pre-determined threshold. An exemplary error counter signal is illustrated in section 206 of FIG. 2. As shown in FIG. 2, the error counter at any instant may be in any one of four possible states. The four possible defined states may include "fail", "not-ready", "pass" and "unknown". More particularly, the error counter may be in the "pass" state when the compared derivatives lie within the pre-determined threshold. For example, if the comparison of a first derivative of the first signal with the derivative of the second signal lies within the pre-determined threshold, the error counter may be in the "pass" state. It should be noted that when in the "pass" state, the behavior of the nitrogen oxide sensor 114 may approximately track the rate of fuel usage of the power source 102.

However, when the compared derivative crosses the pre-determined threshold, the error counter may be triggered, causing the state of the error counter to change to "fail" state. Further, the controller 116 may be configured to increment a count of the error counter based on the number of times the error counter is triggered within a predetermined period of time. Accordingly, the controller 116 may be further configured to determine the condition of the nitrogen oxide sensor 114, based on the count of the error counter. Section 208 of FIG. 2 depicts an exemplary output signal of the controller 116. The determined condition of the nitrogen oxide sensor 114 may include any one of four exemplary states, such as, "fail", "not-ready", "pass" and "unknown".

More specifically, the controller 116 may determine that the nitrogen oxide sensor 114 is in the "pass" state in two situations. The first situation is when the error counter has not been triggered, that is, when the error counter is in the "pass" state. This is indicative of the fact that the compared derivatives lie within the predetermined threshold. The second situation is when the count of the error counter within the predetermined time period does not exceed the predetermined count. For example, if the number of times the state of the error counter has toggled between the "pass" state and the "fail" state does not exceed the predetermined count within the defined time window, the output of the controller 116 may indicate that the nitrogen oxide sensor 114 is in the "pass" state.

On the other hand, if the count of the error counter exceeds the predetermined count within the predetermined period of time, the controller 116 may detect a failure of the nitrogen oxide sensor 114. Accordingly, in this case, the output signal of the controller 116 may be in the "fail" state in order to indicate that the behavior of the nitrogen oxide sensor 114 does not track the rate of fuel usage by the power source 102.

Further, in one embodiment, the controller 116 may notify an operator of the determined condition of the nitrogen oxide sensor 114. For example, the color of an indicator light present in an operator cabin of a machine may change from green to red, on the failure of the nitrogen oxide sensor 114. In another example, a display message may be displayed on a display unit when the failure of the nitrogen oxide sensor 114 is detected. Other such visual and/or auditory feedback associated with the condition of the nitrogen oxide sensor 114 may be provided to the operator, without any limitation.

More specifically, the controller 116 may be configured to determine the erratic and the flat-line failure error of the nitrogen oxide sensor 114. An example of the erratic failure of the nitrogen oxide sensor 114 is illustrated in FIG. 2. As shown in section 206, the error counter monitors the "fail" state five times. The output of the controller 116 is initially in the "not-ready" state (see 208). After a certain delay, the output changes to the "pass" state, indicating that the nitrogen oxide sensor 116 is working satisfactorily. It should be noted that the output continues to remain in the "pass" state even when the error counter has been triggered four times. However, when the error counter is triggered for the fifth time within the predetermined period of time, the output signal changes to the "fail" state. This is indicative of the failure of the nitrogen oxide sensor 114. A person of ordinary skill in the art will appreciate that on observing the behavior of the nitrogen oxide sensor 114 and that of the rate of fuel usage, as seen in 202 and 204, the first signal contains relatively more noise as compared to that of the second signal. Accordingly, such a failure of the nitrogen oxide sensor 114 may be defined as the erratic failure.

Another exemplary situation of the flat-lined error in the nitrogen sensor 114 is depicted in FIG. 3. Section 302 illustrates the first signal received by the controller 116 from the nitrogen oxide sensor 114. The second signal is shown in section 304. The status of the error counter is depicted in section 306. As can be seen, the comparison of the derivatives of the first and second signal results in repeated change in state of the error counter from the "pass" state to the "fail" state, and vice-versa. Accordingly, the failure of the nitrogen oxide sensor 114 is indicated by the output signal shown in 308. One of ordinary skill in the art will appreciate that on observing the behavior of the nitrogen oxide sensor 114 in 302 and that of the rate of fuel usage in 304, it can be inferred that the first signal sensed by the nitrogen oxide sensor 114 is relatively steady or flat-lined as compared to that of the second signal. Such a failure of the nitrogen oxide sensor 114 may be defined as the flat-lined error of the nitrogen oxide sensor 114.

The controller 116 may embody a single microprocessor or multiple microprocessors that includes a means for receiving signals from the nitrogen oxide sensor 114 in order to determine the condition of the nitrogen oxide sensor 114. Numerous commercially available microprocessors may be configured to perform the functions of the controller 116. It should be appreciated that the controller 116 may readily embody a general machine microprocessor capable of controlling numerous machine functions. A person of ordinary skill in the art will appreciate that the controller 116 may additionally include other components and may also perform other functionality not described herein. Further, the connections and sensors described herein are merely on an exemplary basis and do not limit the scope of the disclosure.

Figure 4:
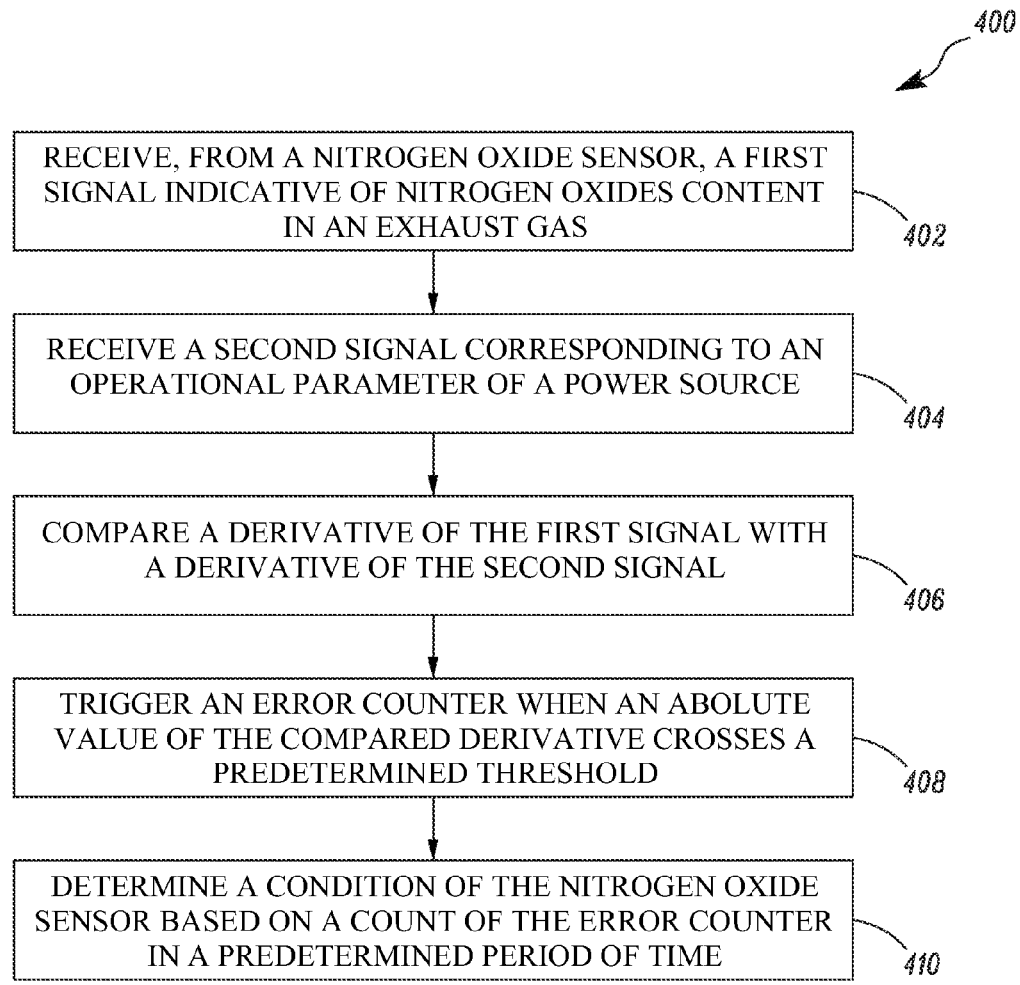
FIG. 4 is a flowchart of a diagnostic method for the nitrogen oxide sensor.

An exemplary diagnostic method 400 for the nitrogen oxide sensor 114 is described in connection with FIG. 4.

INDUSTRIAL APPLICABILITY

Nitrogen oxide sensors may fail due to a variety of reasons, such as for example, overheating, manufacturing defects, and the like. Known diagnostic methods include ascertaining a correspondence between the fuel usage and the nitrogen oxide sensor output. However, these techniques are relatively complex. The present disclosure provides a relatively simplistic diagnostic system and method for determining the condition of the nitrogen oxide sensor.

At step 402, the controller 116 may receive the first signal indicative of the nitrogen oxides content in the exhaust gas from the nitrogen oxide sensor 114. At step 404, the controller 116 may receive the second signal corresponding to the operational parameter of the power source 102. In one embodiment, the operational parameter may include the rate of fuel usage by the power source 102. In the present disclosure, the second signal may be received from the fuel rate sensor 104.

Thereafter, at step 406, the derivative of the first signal may be compared with the derivative of the second signal. If the compared derivative crosses the predetermined threshold, then at step 408, the error counter may be triggered. Further, at step 410, the controller 116 may determine the condition of the nitrogen oxide sensor 114, based on the count of the error counter in the predetermined period of time. In one embodiment, the controller 116 may detect the failure of the nitrogen oxide sensor 114 when the count of the error counter exceeds the predetermined count within the predetermined period of time. The failure of the nitrogen oxide sensor 114 may be either the erratic failure or the flat-lined failure. Additionally, in one embodiment, the controller 116 may notify the operator of the failure of the nitrogen oxide sensor 114. For example, any suitable visual or auditory feedback of the failure of the nitrogen oxide sensor 114 may be provided to the operator.

It should be noted that factors like the predetermined threshold, the predetermined count of the error counter, the predetermined time period associated with the error counter may be fixed or set based on the application and/or experimental data. One of ordinary skill in the art will appreciate that experimentation shows that the rate of fuel corresponds to a relatively higher and more reliable correlation with the nitrogen oxide sensor signal, as compared to other operational factors associated with the power source 102. Further, the rate of fuel usage may be isolated from the SCR module 110, thereby allowing this factor to serve as an unbiased reference for the SCR module components. However, although the present disclosure is described in relation to the rate of fuel usage of the power source 102, other operational parameters related to the power source 102 may also be utilized.

The system described in the present disclosure may be enabled when an exhaust gas recirculation system/actuator faults are inactive, low boost faults are inactive, fuel system related faults are inactive, low nitrogen oxide conversion fault is inactive and other similar faults that are capable of causing low nitrogen oxide conversion condition are inactive.

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:
1. A system comprising:
a nitrogen oxide sensor configured to generate a first signal indicative of, a content of nitrogen oxides in an exhaust gas over time;
a fuel flow sensor configured to generate a second signal indicative of a fuel quantity introduced to an engine over time; and a controller communicably coupled to the nitrogen oxide sensor and the fuel flow sensor, the controller configured to:
- receive, from the nitrogen oxide sensor, the first signal indicative of a content of nitrogen oxides in the exhaust gas over time;
- receive the second signal indicative of a fuel quantity introduced to an internal combustion engine over time;
- subtract a first order time derivative of the first signal from a first order time derivative of the second signal to arrive at a calculated difference;
- trigger an error counter when an absolute value of the calculated difference is greater than a predetermined threshold; and
- determine a condition of the nitrogen oxide sensor based on a count of the error counter in a predetermined period of time; and
- communicate the determined condition of the nitrogen oxide sensor to an operator.

2. The system of claim 1, wherein the controller is further configured to detect a failure of the nitrogen oxide sensor based on if the count of the error counter exceeds a predetermined count within the predetermined period of time.

3. The system of claim 2, wherein the failure is any one of an erratic failure and a flat-lined failure of the nitrogen oxide sensor.

4. A diagnostic method for a nitrogen oxide sensor, the method comprising:
- receiving, from the nitrogen oxide sensor, a first signal indicative of a content of nitrogen oxides in an exhaust gas over time;
- receiving a second signal corresponding to a fuel quantity introduced to an engine over time;
- subtract a first order time derivative of the first signal from a first order time derivative of the second signal to arrive at a calculated difference;
- triggering an error counter when an absolute value of the calculated difference is greater than a predetermined threshold;
- determining a condition of the nitrogen oxide sensor based on a count of the error counter in a predetermined period of time; and
- communicating the determined condition of the nitrogen oxide sensor to an operator.

5. The method of claim 4 further comprising detecting a failure of the nitrogen oxide sensor based on if the count of the error counter exceeds a predetermined count within the predetermined period of time.

6. The method of claim 5, wherein the failure is any one of an erratic failure and a flat-lined failure of the nitrogen oxide sensor.

7. A computer based controller system for diagnosis of a nitrogen oxide sensor, the computer based controller system comprising:
- a communication interface communicating with a memory;
- the memory configured to communicate with a processor; and
- the processor, in response to executing a computer program, performs operations comprising:
  - receiving, from the nitrogen oxide sensor, a first signal indicative of nitrogen oxides content in an exhaust gas;
  - receiving a second signal corresponding to a fuel quantity introduced to an engine over time;
  - subtract a first order time derivative of the first signal from a first order time derivative of the second signal to arrive at a calculated difference;
  - triggering an error counter when an absolute value of the calculated difference is greater than a predetermined threshold;
  - determining a condition of the nitrogen oxide sensor based on a count of the error counter in a predetermined period of time; and
  - communicating the determined condition of the nitrogen oxide sensor to an operator.

8. The computer based controller system of claim 7, wherein the operations performed by the processor further comprises detecting a failure of the nitrogen oxide sensor based on if the count of the error counter exceeds a predetermined count within the predetermined period of time.

9. The computer based controller system of claim 8, wherein the failure is any one of an erratic failure and a flat-lined failure of the nitrogen oxide sensor.

* * * * *